United States Patent [19]

Mori et al.

[11] Patent Number: 5,374,758

[45] Date of Patent: Dec. 20, 1994

[54] HYDRO-TERMINATED POLYSILANE AND PROCESS FOR MAKING

[75] Inventors: Shigeru Mori; Eiichi Tabei, both of Kawasaki, Japan

[73] Assignee: Shin-Etsu Chemical Co., Ltd., Tokyo, Japan

[21] Appl. No.: 96,259

[22] Filed: Jul. 26, 1993

[30] Foreign Application Priority Data

Jul. 30, 1992 [JP]  Japan .................................. 4-223372

[51] Int. Cl.$^5$ ................................................. C07F 7/08
[52] U.S. Cl. ........................................................ 556/430
[58] Field of Search .......................................... 556/430

[56] References Cited

U.S. PATENT DOCUMENTS

| | | | |
|---|---|---|---|
| 3,146,249 | 8/1964 | Alsgaard et al. | 556/430 |
| 4,052,430 | 10/1977 | Yajima et al. | 556/430 |
| 4,461,908 | 7/1984 | Takamizawa et al. | 556/430 |
| 4,537,942 | 8/1985 | Brown-Wensley et al. | 556/430 X |
| 4,611,035 | 9/1986 | Brown-Wensley et al. | 556/430 X |
| 4,704,444 | 11/1987 | Brown-Wensley et al. | 556/430 X |
| 4,900,861 | 2/1990 | Yokoyama et al. | 556/430 |
| 5,003,100 | 3/1991 | Berris et al. | 556/430 |
| 5,047,569 | 9/1991 | Berris et al. | 556/430 |
| 5,229,481 | 7/1993 | Tilley | 556/430 X |
| 5,252,766 | 10/1993 | Sakakura et al. | 556/430 |

OTHER PUBLICATIONS

Journal of Polymer Science: Polymer Chemistry Edition, vol. 22, 159–170 (1984).
Journal of Organometallic Chemistry, vol. 300, 327 (1986).
Journal of Polymer Science: Polymer Letter Edition, vol. 21, 819 (1983).
Kagaku to Kogyo (Chemistry & Industry), vol. 42, No. 4, 744.
Journal of Organometallic Chemistry, vol. 2, 478–484 (1964).
Journal of Organometallic Chemistry, vol. 23, 63–69 (1970).
Applied Organometallic Chemistry, vol. 1, 7–14 (1987).

*Primary Examiner*—Paul F. Shaver
*Attorney, Agent, or Firm*—Birch, Stewart, Kolasch & Birch

[57] ABSTRACT

A both end hydro-terminated polysilane is of the formula: $H[(R^1R^2Si)_n(R^3R^4Si)_m]_kH$ wherein $R^1$, $R^2$, $R^3$ and $R^4$ are independently $C_1$–$C_{12}$ alkyl groups or aryl groups and letters n, m and k are numbers in the range: $0 \leq n \leq 10$, $0 \leq m \leq 10$, $n+m \geq 10$, and $k \geq 1$. It is prepared by dissolving a corresponding chloro-terminated polysilane in a solvent and reducing with $LiAlH_4$ in an inert gas atmosphere.

12 Claims, 1 Drawing Sheet

HYDRO-TERMINATED POLYSILANE AND PROCESS FOR MAKING

BACKGROUND OF THE INVENTION

1. Field of the Invention

This invention relates to a both end hydro-terminated polysilane capable of accepting any desired functional group and useful as a source material for forming copolymers with other polymers as well as process for preparing the same.

2. Prior Art

Most industrial processes for preparing polysilanes utilize coupling reaction of dihalogenosilanes with alkali metals as reported in Journal of Polymer Science: Polymer Chemistry Edition, Vol. 22, 159–170 (1984), Journal of Organometallic Chemistry, Vol. 300, 327 (1986), and Journal of Polymer Science: Polymer Letter Edition, Vol. 21, 819 (1983). These processes produce polysilanes in the form of mixtures of cyclic polymers and halo- or hydrogen-terminated polymers. It is difficult to quantitatively obtain terminally modified polymers from these mixtures.

With respect to the synthesis of single end modified polysilanes, Sakurai et al. attempt living polymerization from polymers containing a disilane unit for introducing hydrogen or carboxylic acid as well as copolymerization of such polymers with polymethyl methacrylate (PMMA) as reported in Kagaku to Kogyo (Chemistry and Industry), Vol. 42, No. 4, 744. This attempt, however, has several industrial problems including limited type of substituents and limited availability of monomers.

Exemplary synthesis of both and single end reactive polysilanes is reported in Journal of Organometallic Chemistry, Vol. 2, 478–484 (1964) and Journal of Organometallic Chemistry, Vol. 23, 63–69 (1970). More specifically, chloro-terminated oligosilanes can be prepared by reacting permethyloligosilanes with acetyl chloride in the presence of aluminum chloride. Also chloro-terminated oligosilanes can be prepared by reacting phenyl-terminated oligosilanes with hydrogen chloride or chlorosilane in the presence of aluminum chloride. These chloro-terminated oligosilanes, however, have a low degree of polymerization.

SUMMARY OF THE INVENTION

Therefore, an object of the present invention is to provide a novel and improved hydro-terminated polysilane with a high degree of polymerization capable of accepting any desired functional group and suitable as a source material for forming copolymers with other polymers. Another object is to provide a process for preparing such a hydro-terminated polysilane.

The inventors have found that by reacting a both end chloro-terminated polysilane with LiAlH$_4$ for reducing the polysilane, there is obtained a both end hydro-terminated polysilane having a high degree of polymerization which has never been reported of synthesis.

Focusing on the reaction that on exposure to ultraviolet (UV) radiation, polysilanes decompose and convert to those of a lower molecular weight while yielding highly reactive silylene and silyl radicals as reported in Applied Organometallic Chemistry, Vol. 1, 7–14 (1987), the inventors found that when high-molecular weight polysilanes are photo-decomposed by selecting a chlorinated hydrocarbon as a solvent prone to chlorine withdrawal and exposing the polysilanes to UV radiation in the chlorinated hydrocarbon, silyl radicals generate and then form chloro-terminated polysilanes having a high degree of polymerization (see Japanese Patent Application No. 30103/1992 or U.S. Ser. No. 08/006,487 filed on Jan. 21, 1993). The inventors have found that by reducing such a chloro-terminated polysilane of formula (2) defined below with LiAlH$_4$, there is obtained a hydro-terminated polysilane of formula (1) defined below. This hydro-terminated polysilane has reactive hydrogen atoms at both ends, allowing any desired functional group to be introduced into the polysilane by using well-known reaction processes, for example, addition reaction with a —CH=CH$_2$ group and condensation reaction with a —OH group or allowing other polymers to copolymerize therewith for forming copolymers. Therefore, the hydro-terminated polysilane is a useful source material for polysilanes finding use in such applications as photoconductive materials, conductive materials, photoresists, ceramics, and non-linear optical materials.

Accordingly, the present invention provides a both end hydro-terminated polysilane of formula (1). The present invention also provides a process for preparing a both end hydro-terminated polysilane of formula (1) by dissolving a both endchloro-terminated polysilane of formula(2) in a suitable solvent and reducing the polysilane with LiAlH$_4$ in an inert atmosphere according to the following scheme.

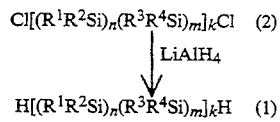

In the formula, R$^1$, R$^2$, R$^3$ and R$^4$ are independently substituted or unsubstituted alkyl groups having 1 to 12 carbon atoms or aryl groups, letters n, m and k are numbers in the range: $0 \leq n \leq 10$, $0 \leq m \leq 10$, $n+m \geq 10$, and $k \geq 1$.

BRIEF DESCRIPTION OF THE DRAWING

The only figure.

DETAILED DESCRIPTION OF THE INVENTION

Figure 1:
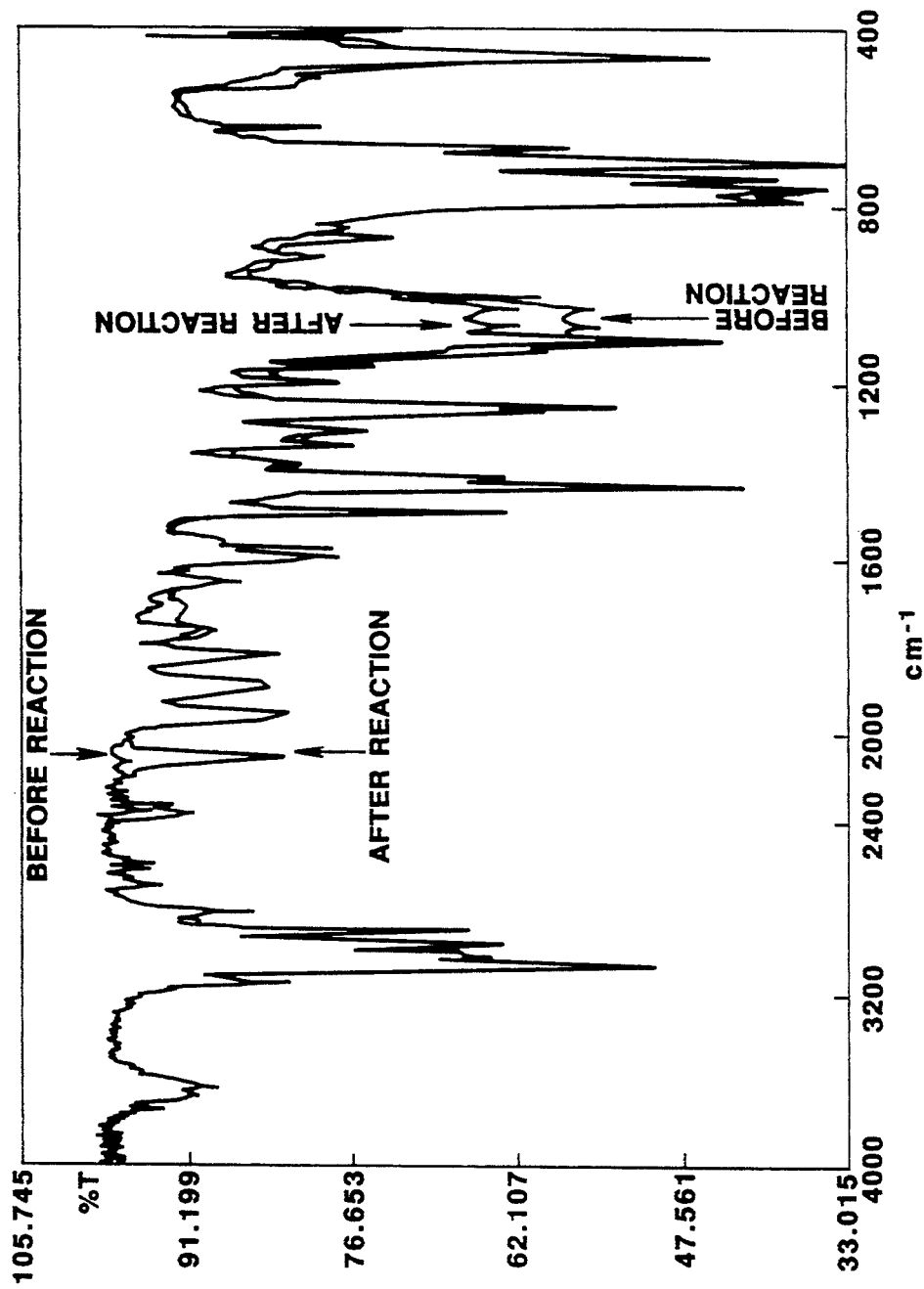
FIG. 1 is a chart showing IR absorption spectraof the hydro-terminated polysilane of Example 1.

The hydro-terminated polysilane of the present invention is represented by formula (1).

In formula (1), R$^1$, R$^2$, R$^3$ and R$^4$, which may be identical or different, are substituted or unsubstituted alkyl groups having 1 to 12 carbon atoms, preferably 1 to 8 carbon atoms or substituted or unsubstituted aryl groups. The preferred alkyl groups are lower alkyl groups such as methyl, ethyl and propyl groups and the aryl groups include phenyl, tolyl and styryl groups. Letters n, m an k are numbers in the range: $0 \leq n \leq 10$, $0 \leq m \leq 10$, $n+m \geq 10$, and $k \geq 1$. Preferably, k is 5 or more, especially 10 or more, in order that the polysilane exert photoconductivity and other desired properties. The term hydro-terminated means that the polysilane is terminated with hydrogen a both ends of its molecular chain unless otherwise stated.

According to the invention, the hydro-terminated polysilane of formula (1) is prepared by dissolving a chloro-terminated polysilane of formula (2) in a suitable solvent and reacting the polysilane with LiAlH$_4$ in an inert atmosphere for reduction.

In the formula, R$^1$ to R$^4$, n, m and k are as defined above.

The starting material or chloro-terminated polysilane can be prepared by the process of our patent application (Japanese Patent Application No. 101804/1992 or U.S. Ser. No. 08/006,487 filed on Jan. 21, 1993).

More specifically, the chloro-terminated polysilane of formula (2) is prepared by first effecting coupling reaction of a dichlorosilane with an alkali metal such as sodium for forming a polysilane of formula (3), preferably having a number average molecular weight (Mn) of 1,000 or higher. Next, the polysilane is dissolved in a chlorinated hydrocarbon solvent (e.g., dichloromethane, chloroform, carbon tetrachloride, 1,2-dichloroethane, 1,1,2-tri-chloroethane, and 1,1,2,2-tetrachloroethane) preferably at a concentration of about 1 to 20% by weight and exposed to UV radiation in an inert gas atmosphere (e.g., nitrogen and argon gas). After exposure to a predetermined dose of UV, the reaction solution is concentrated to ½ to 1/5 in volume. Hexane is added to the concentrate such that about 150 grams of hexane is available per 10 grams of the polysilane, thereby causing the chloro-terminated polysilane (Mn≧1,000) to precipitate. Through filtration and drying, the end chloro-terminated polysilane is obtained as white powder.

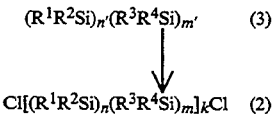

R$^1$ to R$^4$, n, m and k are as defined above, n'≧0, m'≧0 and n'+m'≧1.

The thus obtained chloro-terminated polysilane of formula (2) is dissolved in a solvent such as ethers and tetrahydrofuran (THF), preferably at a concentration of 5 to 50% by weight, especially 10 to 30% by weight and reacted with LiAlH$_4$ in an inert gas atmosphere such as nitrogen and argon gas. Preferably about 0.25 to 2 mol, especially about 1 to 20 mol of LiAlH$_4$ is used per mol of chlorine in the chloro-terminated polysilane of formula (2). The reaction temperature is between room temperature and the reflux temperature of the solvent (e.g., 65° C. for THF) and the reaction time is usually about 1 to 4 hours.

After the chloro-terminated polysilane is reduced, the unreacted LiAlH$_4$ is deactivated with alcohol. The reaction mixture is washed with water several times and the organic layer is taken out, dried, and concentrated. There is obtained an end product, that is a hydro-terminated polysilane of formula (1) as white powder.

The hydro-terminated polysilane has a high degree of polymerization and a reactive hydrosilyl group at each end to which a substituent can be attached. Then the hydro-terminated polysilane is a useful source material for subsequent crosslinking reaction.

There has been described hydro-terminated polysilane having a reactive hydrosilyl group at each end which allows introduction of any desired functional group and copolymerization with other polymers for forming copolymers.

EXAMPLE

Examples of the present invention are given below by way of illustration and not by way of limitation. All parts and percents are by weight. Mn and Mw are number and weight average molecular weights, respectively.

Example 1

In a nitrogen gas atmosphere, 5.5 grams of chloro-terminated methylphenylpolysilane (Mn=5,500, Mw/Mn=1.90) was dissolved in 50 grams of THF, and 0.15 grams of LiAlH$_4$ was added to the solution. Agitation was continued for 4 hours. At the end of reaction, 5 grams of methanol was added to the reaction mixture, which was washed with 100 grams of water three times. The organic layer was dried overnight over calcium chloride. After the desiccant was filtered off, the solution was concentrated, yielding 3.5 grams of white powder. Measurements of this white powder are shown below.

Yield: about 64%
Mn: 5,450 (calculated as polystyrene)
Mw/Mn: 1.86
IR analysis: 2098 cm$^{-1}$ (Si-H) intense peak
Cl concentration: 0%
Proton-NMR:
  Si-Me—0.8 to 0.7 ppm (integration ratio 330)
  Si-H 4.4 ppm (integration ratio 2)
  Ph 6.3 to 7.8 ppm (integration ratio 734, including benzene in measurement solvent d6-benzene)

These measurements imply that the white powder is a both end hydro-terminated methyl-phenylpolysilane. By calculating the degree of polymerization from the integration ratios of Si-Me and Si-H, it was identified to be a compound of formula (1a).

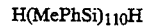

wherein Me is methyl and Ph is phenyl.

FIG. 1 is a chart showing IR absorption spectra of the hydro-terminated polysilane. In FIG. 1, "before reaction" is the spectra of the starting chloro-terminated polysilane and "after reaction" is the spectra of the resulting hydro-terminated polysilane.

Example 2

In a nitrogen gas atmosphere, 20.0 grams of chloro-terminated methylphenylpolysilane (Mn=7,500, Mw/Mn=2.0) was dissolved in 200 grams of THF, and 0.5 grams of LiAlH$_4$ was added to the solution. Agitation was continued for 4 hours. At the end of reaction, 20 grams of methanol was added to the reaction mixture, which was washed with 200 grams of water three times. The organic layer was dried overnight over calcium chloride. After the desiccant was filtered off, the solution was concentrated, yielding 15.8 grams of white powder. Measurements of this white powder are shown below.

Yield: about 79%
Mn: 7,350 (calculated as polystyrene)
Mw/Mn: 1.96
IR analysis: 2098 cm$^{-1}$ (Si-H) intense peak
Cl concentration: 0%
Proton-NMR:

Si-Me—0.8 to 0.7 ppm (integration ratio 400)
Si-H 4.4 ppm (integration ratio 2)
Ph 6.3 to 7.8 ppm (integration ratio 880, including benzene in measurement solvent d6-benzene)

These measurement imply that the white powder is a both end hydro-terminated methylphenylpolysilane. By calculating the degree of polymerization from the integration ratios of Si-Me and Si-H, it was identified to be a compound of formula (1b).

$$H(MePhSi)_{133}H \tag{1b}$$

Reference Example 1

Methylphenylpolysilane having Mn=24,000 and Mw/Mn=3.32 was previously prepared by coupling reaction of methylphenyldichlorosilane with sodium. 7.0 grams of methylphenylpolysilane was dissolved in 133 grams of carbon tetrachloride to a concentration of 5%. In a nitrogen gas atmosphere, a Pyrex reaction tube with a diameter of 15 mm was filled with the polysilane solution, closed with a plug, and exposed to UV radiation (312 nm) in a dose as shown in Table 1 using a high-pressure mercury lamp. The reaction solution was concentrated to about 50 grams. Addition of 100 grams of hexane to the solution caused precipitation. The precipitate was isolated by filtration and dried, obtaining a white powder. It was identified to be a chloro-terminated polysilane of the following formula (4) from its molecular weight, yield and chlorine content (measured by titration) as reported in Table 1.

$$Cl-(CH_3C_6H_5Si)_6-Cl \tag{4}$$

TABLE 1

| Run No. | UV dose (J/cm²) | Chloro-terminated polysilane | | | | |
|---|---|---|---|---|---|---|
| | | Mn | Mw/Mn | Yield (%) | Cl (%) Found | Cl (%) Calc. |
| 1 | 1 | 15,970 | 2.34 | 77 | 0.45 | 0.45 |
| 2 | 2 | 12,220 | 1.94 | 65 | 0.54 | 0.58 |
| 3 | 3 | 11,980 | 1.93 | 63 | 0.58 | 0.59 |
| 4 | 5 | 8,300 | 1.70 | 60 | 0.84 | 0.86 |
| 5 | 10 | 4,600 | 1.47 | 52 | 1.49 | 1.53 |

Reference Example 2

Methylphenylpolysilane having Mn=15,900 and Mw/Mn=10 was previously prepared by coupling reaction of methylphenyldichlorosilane with sodium. 0.5 grams of methylphenylpolysilane was dissolved in 9.5 grams of a chlorinated hydrocarbon as shown in Table 2. The solution had a concentration of 5%. In a nitrogen gas atmosphere, a Pyrex reaction tube with a diameter of 15 mm was filled with the polysilane solution, closed with a plug, and exposed to UV radiation (312 nm) in a dose as shown in Table 2 using a high-pressure mercury lamp. The reaction solution was concentrated to about 2 grams. Addition of 20 grams of hexane to the solution caused precipitation. The precipitate was isolated by filtration and dried, obtaining a chloro-terminated polysilane as a white powder. Measurement of the products are shown in Table 2.

TABLE 2

| No. | Methylphenyl-dichlorosilane | Solvent Type | Amount (g) | UV dose (J/cm²) | Chloro-terminated polysilane | | | | |
|---|---|---|---|---|---|---|---|---|---|
| | | | | | Molecular weight Mn* | Mw/Mn | Cl content (ppm) Found | Cl content (ppm) Calc. | Yield (%) |
| 6 | 0.5 | dichloromethane | 9.5 | 0.5 | 13,500 | 4.94 | 4900 | 5260 | 82 |
| 7 | 0.5 | dichloromethane | 9.5 | 1.0 | 10,800 | 3.59 | 6200 | 6570 | 74 |
| 8 | 0.5 | 1,2-dichloroethane | 9.5 | 0.5 | 15,000 | 7.00 | 4300 | 4730 | 76 |
| 9 | 0.5 | 1,2-dichloroethane | 9.5 | 1.5 | 11,500 | 6.05 | 5500 | 6170 | 64 |
| 10 | 0.5 | chloroform | 9.5 | 0.5 | 13,300 | 4.51 | 5000 | 5340 | 71 |
| 11 | 0.5 | 1,1,2-trichloroethane | 9.5 | 0.5 | 13,000 | 5.20 | 5100 | 5460 | 65 |
| 12 | 0.5 | 1,1,2,2-tetrachloroethane | 9.5 | 0.5 | 12,100 | 4.82 | 5300 | 5870 | 74 |

*calculated as polystyrene

Although some preferred embodiments have been described, many modifications and variations may be made thereto in the light of the above teachings. It is therefore to be understood that within the scope of the appended claims, the invention may be practiced otherwise than as specifically described.

We claim:

1. A hydro-terminated polysilane of the following formula (1):

$$H((R^1R^2Si)_n(R^3R^4Si)_m)_kH \tag{1}$$

wherein $R^1$, $R^2$, $R^3$ and $R^4$ are independently selected from substituted or unsubstituted alkyl groups having 1 to 12 carbon atoms and aryl groups, letters n, m and k are numbers in the range: $0 \leq n \leq 10$, $0 \leq m \leq 10$, $n+m \geq 10$, and $k \geq 5$.

2. The hydro-terminated polysilane according to claim 1, wherein $R^1$, $R^2$, $R^3$ and $R^4$ are independently selected from substituted or unsubstituted alkyl groups having 1 to 8 carbon atoms.

3. The hydro-terminated polysilane according to claim 1, wherein $R^1$, $R^2$, $R^3$ and $R^4$ are independently selected from the group consisting of substituted or unsubstituted methyl, ethyl and propyl groups.

4. The hydro-terminated polysilane according to claim 1, wherein $R^1$, $R^2$, $R^3$ and $R^4$ are independently selected from the group consisting of substituted or unsubstituted phenyl, tolyl and styryl groups.

5. A process for preparing a hydro-terminated polysilane, comprising the step of reducing with LiAlH$_4$ a chloro-terminated polysilane of the following formula (2):

$$Cl[(R^1R^2Si)_n(R^3R^4Si)_m]_kCl \tag{2}$$

wherein $R^1$, $R^2$, $R^3$ and $R^4$ are independently selected from substituted or unsubstituted alkyl groups having 1 to 12 carbon atoms and aryl groups, letters n, m and k are numbers in the range: $0 \leq n \leq 10$, $0 \leq m \leq 10$, $n+m \geq 10$, and $k \geq 1$.

6. The process for preparing a hydro-terminated polysilane according to claim 5, wherein $k \geq 5$.

7. The process for preparing a hydro-terminated polysilane according to claim 2, wherein said chloro-terminated polysilane of formula (2) is dissolved in a solvent selected from the group consisting of ethers and tetrahydrofuran prior to reaction with said LiAlH$_4$.

8. The process for preparing a hydro-terminated polysilane according to claim 5, wherein said chloro-terminated polysilane of formula (2) is reacted with said LiAlH$_4$ in an inert gas atmosphere.

9. The process for preparing a hydro-terminated polysilane according to claim 3, wherein said inert gas atmosphere is nitrogen or argon gas.

10. The process for preparing a hydro-terminated polysilane according to claim 5, wherein 0.25 to 2 mol LiAlH$_4$ is used per mol chlorine in said chloro-terminated polysilane.

11. The process for preparing a hydro-terminated polysilane according to claim 5, wherein 1 to 20 mol LiAlH$_4$ is used per mol chlorine in said chloro-terminated polysilane.

12. The process for preparing a hydro-terminated polysilane according to claim 7, wherein the reaction temperature is between room temperature and the reflux temperature of said solvent and the reaction time is from 1 to 4 hours.

* * * * *